(12) United States Patent
Wasserman

(10) Patent No.: US 12,114,991 B2
(45) Date of Patent: Oct. 15, 2024

(54) VARYING THE METALLIZATION AREA ON INDIVIDUAL ELECTRODE ELEMENTS IN A TUMOR TREATING FIELDS (TTFIELDS) SYSTEM TO MAXIMIZE CURRENT WITHOUT OVERHEATING

(71) Applicant: Novocure GmbH, Root (CH)

(72) Inventor: Yoram Wasserman, Haifa (IL)

(73) Assignee: Novocure GmbH, Root (CH)

( * ) Notice: Subject to any disclaimer, the term of this patent is extended or adjusted under 35 U.S.C. 154(b) by 601 days.

(21) Appl. No.: 17/478,189

(22) Filed: Sep. 17, 2021

(65) Prior Publication Data
US 2022/0095997 A1 Mar. 31, 2022

Related U.S. Application Data

(60) Provisional application No. 63/083,590, filed on Sep. 25, 2020.

(51) Int. Cl.
*A61B 5/00* (2006.01)
*A61N 1/04* (2006.01)
*A61N 1/32* (2006.01)

(52) U.S. Cl.
CPC ............ *A61B 5/441* (2013.01); *A61N 1/0476* (2013.01); *A61N 1/0492* (2013.01); *A61N 1/326* (2013.01)

(58) Field of Classification Search
CPC .... A61B 5/441; A61N 1/0476; A61N 1/0492; A61N 1/326; A61N 1/40; A61N 1/36002
See application file for complete search history.

(56) References Cited

U.S. PATENT DOCUMENTS

| | | | |
|---|---|---|---|
| 6,868,289 B2 | 3/2005 | Palti |
| 7,016,725 B2 | 3/2006 | Palti |
| 7,089,054 B2 | 8/2006 | Palti |
| 7,136,699 B2 | 11/2006 | Palti |

(Continued)

FOREIGN PATENT DOCUMENTS

| | | | |
|---|---|---|---|
| WO | 2020104921 A1 | 5/2020 |
| WO | 2020110050 A1 | 6/2020 |

OTHER PUBLICATIONS

International Search Report and Written Opinion issued in application No. PCT/IB2021/058514 dated Jan. 4, 2022.

*Primary Examiner* — Yi-Shan Yang
*Assistant Examiner* — Joseph A Tombers
(74) *Attorney, Agent, or Firm* — Potomac Law Group, PLLC

(57) ABSTRACT

Conventional transducer arrays for applying tumor treating fields (TTFields) include a set of individual electrode elements, and the more peripherally-located electrode elements (e.g., electrode elements at the corners or edges of the transducer arrays) tend to get hotter than the more centrally located electrode elements. This situation can be ameliorated by reducing the capacitance of the more peripherally-located electrode elements. Reducing the capacitance of those elements reduces the current that travels through those elements (at any given voltage), which reduces the temperature of those elements. Once the capacitance of the more peripherally-located electrode elements is reduced, higher voltages can be used without overheating. This leads to an increase in the overall current, which can improve the efficacy of the TTFields treatment.

20 Claims, 10 Drawing Sheets

(56) References Cited

U.S. PATENT DOCUMENTS

| | | |
|---|---|---|
| 7,146,210 B2 | 12/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 10,779,875 B2 | 9/2020 | Palti et al. |
| 10,821,283 B2 | 11/2020 | Giladi et al. |
| 10,953,209 B2 | 3/2021 | Story et al. |
| 10,967,167 B2 | 4/2021 | Hagemann et al. |
| 11,013,909 B2 | 5/2021 | Wenger et al. |
| 11,020,585 B2 | 6/2021 | Alon et al. |
| 11,097,101 B2 | 8/2021 | Wasserman et al. |
| 11,103,698 B2 | 8/2021 | Chang et al. |
| 11,109,773 B2 | 9/2021 | Urman et al. |
| 11,154,707 B2 | 10/2021 | Bomzon et al. |
| D934,892 S | 11/2021 | Hershkovich et al. |
| 11,160,977 B2 | 11/2021 | Naveh et al. |
| 11,179,322 B2 | 11/2021 | Gotlib et al. |
| 2006/0167499 A1 | 7/2006 | Palti |
| 2007/0239213 A1 | 10/2007 | Palti |
| 2009/0076366 A1 | 3/2009 | Palti |
| 2011/0137229 A1 | 6/2011 | Palti et al. |
| 2011/0301683 A1* | 12/2011 | Axelgaard ........... A61N 1/0492 607/149 |
| 2012/0283726 A1 | 11/2012 | Palti |
| 2016/0045755 A1* | 2/2016 | Chun ..................... A61F 7/10 607/101 |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Gilladi et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0016399 A1 | 1/2020 | Kaynan et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0114141 A1 | 4/2020 | Bomzon et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0179512 A1 | 6/2020 | Giladi et al. |
| 2020/0219261 A1 | 7/2020 | Shamir et al. |
| 2020/0306531 A1 | 10/2020 | Tran et al. |
| 2020/0330755 A1 | 10/2020 | Wasserman et al. |
| 2020/0368525 A1 | 11/2020 | Maag et al. |
| 2021/0031031 A1 | 2/2021 | Wasserman et al. |
| 2021/0038584 A1 | 2/2021 | Voloshin-Sela |
| 2021/0060334 A1 | 3/2021 | Avraham et al. |
| 2021/0069503 A1 | 3/2021 | Tran et al. |
| 2021/0187277 A1 | 6/2021 | Wasserman et al. |
| 2021/0196348 A1 | 7/2021 | Wasserman |
| 2021/0199640 A1 | 7/2021 | Patel et al. |
| 2021/0203250 A1 | 7/2021 | Wasserman |
| 2021/0268247 A1 | 9/2021 | Story et al. |
| 2021/0299440 A1 | 9/2021 | Deslauriers et al. |
| 2021/0308446 A1 | 10/2021 | Alon et al. |
| 2021/0330950 A1 | 10/2021 | Hagemann et al. |
| 2021/0346694 A1 | 11/2021 | Wasserman et al. |
| 2021/0379362 A1 | 12/2021 | Smith et al. |

\* cited by examiner

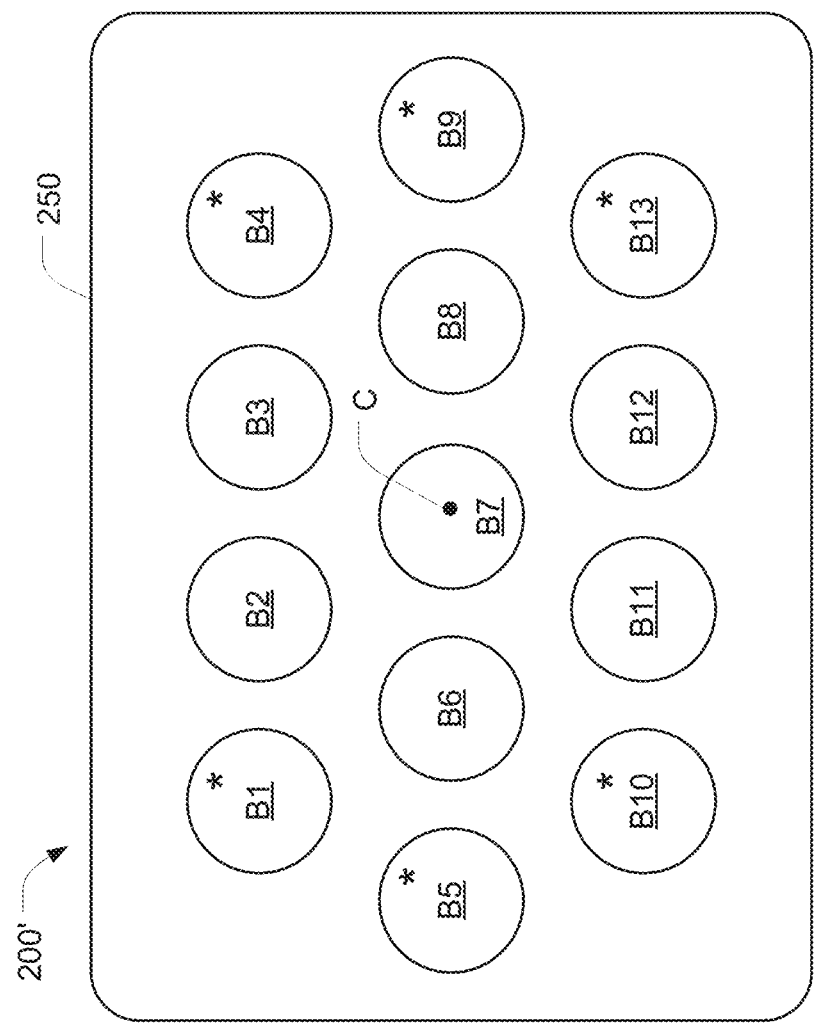

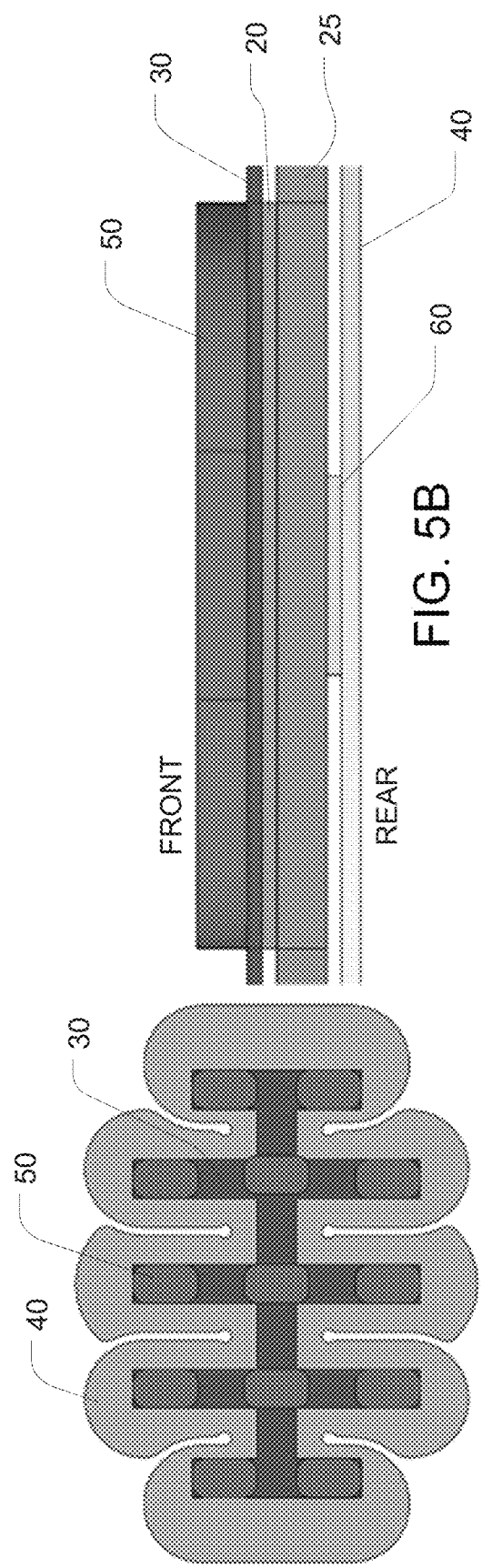

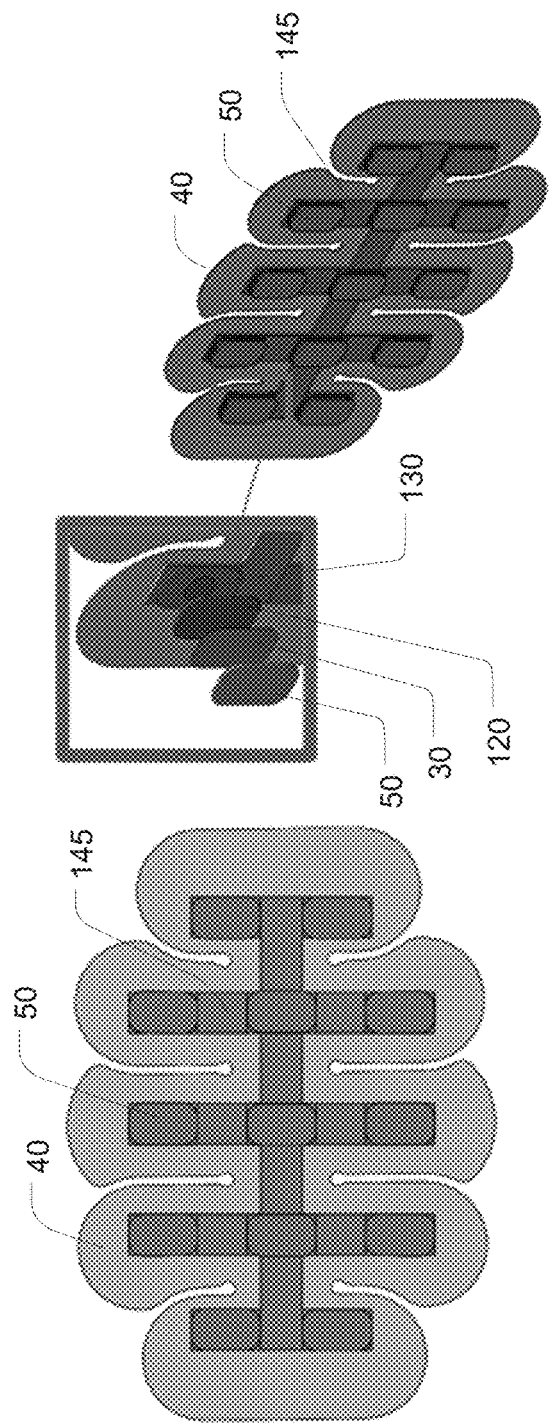
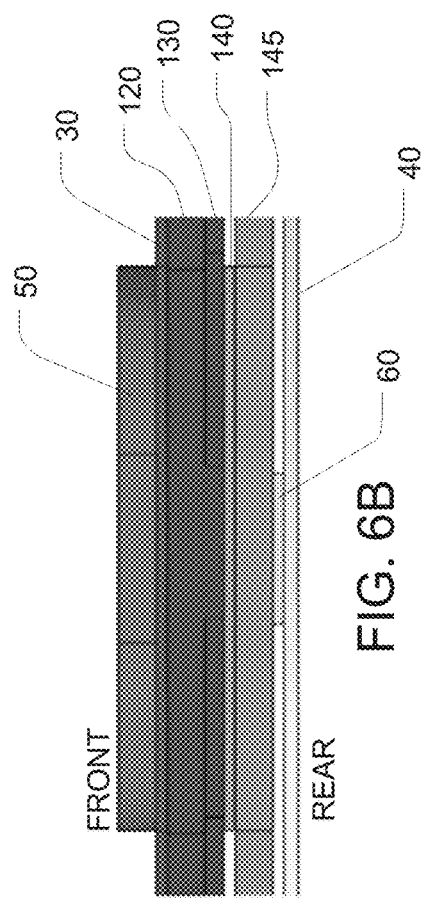
FIG. 6A
FIG. 6B
FIG. 6C

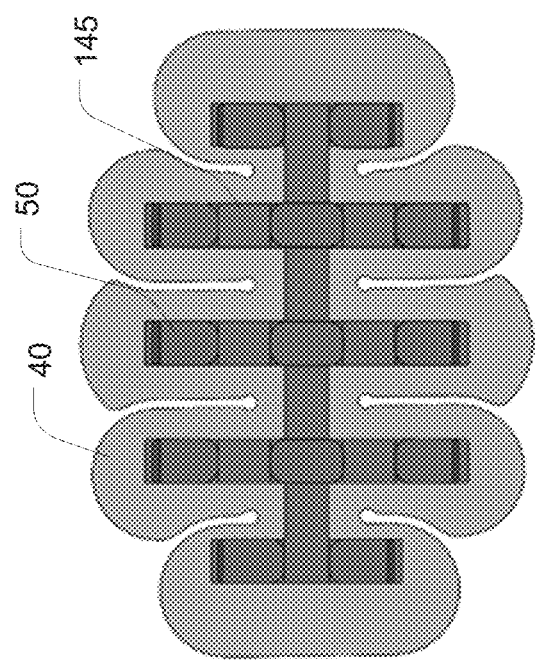
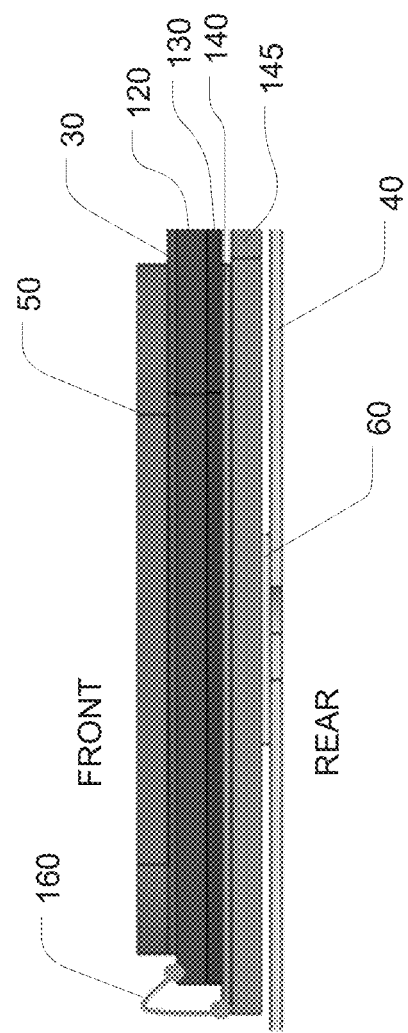
FIG. 7A
FIG. 7B

VARYING THE METALLIZATION AREA ON INDIVIDUAL ELECTRODE ELEMENTS IN A TUMOR TREATING FIELDS (TTFIELDS) SYSTEM TO MAXIMIZE CURRENT WITHOUT OVERHEATING

CROSS-REFERENCE TO RELATED APPLICATIONS

This application claims the benefit of U.S. Application No. 63/083,590 filed Sep. 25, 2020, the entire disclosure of which is incorporated herein by reference in its entirety.

BACKGROUND

U.S. Pat. Nos. 7,136,699 and 7,146,210, each of which is incorporated herein by reference, describe treating tumors or other rapidly dividing cells with AC electric fields at particular frequencies and field strengths. These AC electric fields are referred to herein as "tumor treating fields" or "TTFields."

U.S. Pat. No. 8,715,203 describes a prior art "composite electrode" (also referred to as a "transducer array") that is used for applying TTFields. The transducer array of the '203 patent is depicted in FIG. 1, and it includes 9 round electrode elements, each of which comprises a ceramic element (e.g. a ceramic disk) which measures about 2 cm in diameter. One side of each ceramic element faces the skin of the subject, and the other side has a conductive backing (e.g., is silvered). A flex circuit connects the silvered backs of all of the ceramic elements on any given transducer array to a single lead. And a layer of hydrogel is disposed between each of the ceramic elements and the subject's skin.

When a first transducer array is positioned against a person's skin on one side of a person's body, and a second transducer array is positioned against the person's skin on the opposite side of the person's body, and an AC voltage is applied between the leads of the first and second transducer arrays, an electric current is capacitively coupled into the person's body. For TTFields to be effective, a sufficient amount of current must be capacitively coupled through the electrodes and into the person's body; and higher currents are strongly correlated with higher efficacy of treatment. Because increasing the capacitance of each of the transducer arrays results in a corresponding increase of current, prior art transducer arrays typically used relatively thin ceramic elements (e.g., about 1 mm thick ceramic disks) with very high dielectric constants (e.g., >1000) in order to achieve sufficiently high currents.

The ceramic elements heat up during use; and safety considerations require that the temperature at each of the ceramic elements remain below a specific safety threshold (e.g., 41° C.).

When all the ceramic elements in any given transducer array are wired in parallel, if the temperature at any one of the ceramic elements on a given transducer array gets too high, the voltage that is applied to that entire transducer array must be lowered to prevent the temperature of the hottest element from exceeding the safety threshold. (In the '203 patent, the temperature readings are obtained using a plurality of thermistors, each of which is positioned in the center of a respective ceramic element.) Assume, for example, that the temperature of a single one of the ceramic elements in the FIG. 1 prior art system rises to 41° C., but the temperature of the remaining 8 ceramic elements is only 39° C. In this situation, even though the average temperature of the electrode elements is $((8\times39)+41)/9=39.2°$ C., the voltage that is applied to the transducer array must be reduced to prevent the hottest element from overheating. And this reduction in voltage leads to a reduction in current, which can reduce the efficacy of the treatment.

SUMMARY OF THE INVENTION

One aspect of the invention is directed to a first apparatus for applying an alternating electric field to a living subject. The first apparatus comprises a plurality of conductive regions, a plurality of regions of a dielectric material, a substrate, and at least one electrical conductor. Each of the conductive regions has a front face and a respective area. Each of the regions of dielectric material has (i) a respective front face and (ii) a respective rear face disposed against the front face of a respective one of the conductive regions. The substrate is configured to hold the front faces of the plurality of regions of dielectric material on or in the subject's body and support the plurality of conductive regions at respective positions distributed about a centroid. And the at least one electrical conductor is disposed in electrical contact with the plurality of conductive regions. The plurality of conductive regions includes at least one first conductive region and a plurality of second conductive regions, and each of the second conductive regions is positioned more peripherally with respect to the centroid than the at least one first conductive region. The area of each of the second conductive regions is at least 10% smaller than the area of each of the first conductive regions.

In some embodiments of the first apparatus, each of the regions of the dielectric material comprises a ceramic disk, and each of the plurality of the conductive regions comprises a layer of metal disposed on the rear face of a respective one of the ceramic disks. In some embodiments of the first apparatus, each of the regions of the dielectric material comprises a flat piece of ceramic material, and each of the plurality of the conductive regions comprises a layer of metal disposed on the rear face of a respective one of the pieces of ceramic material.

In some embodiments of the first apparatus, each of the plurality of the conductive regions comprises a pad of a printed circuit, and each of the regions of the dielectric material comprises a polymer film. In some embodiments of the first apparatus, each of the plurality of the conductive regions comprises a pad of a printed circuit, and each of the regions of the dielectric material is implemented using a different section of a single, contiguous, polymer film. In some embodiments of the first apparatus, each of the plurality of the conductive regions comprises a layer of metal foil, and each of the regions of the dielectric material comprises a polymer film. In some embodiments of the first apparatus, each of the plurality of the conductive regions comprises a layer of metal foil, and each of the regions of the dielectric material is implemented using a different section of a single, contiguous, polymer film.

Some embodiments of the first apparatus further comprise an adhesive layer configured to hold the substrate against a person's skin so that the front faces of the plurality of regions of dielectric material face the subject's body.

In some embodiments of the first apparatus, the plurality of conductive regions comprises: at least one first conductive region, and a plurality of second conductive regions, and a plurality of third conductive regions, wherein each of the third conductive regions is positioned more peripherally with respect to the centroid than the plurality of second conductive regions, and wherein the area of each of the third conductive regions is at least 10% smaller than the area of each of the second conductive regions, and wherein each of the second conductive regions is positioned more peripherally with respect to the centroid than the at least one first conductive region, and wherein the area of each of the second conductive regions is at least 10% smaller than the area of each of the first conductive regions.

Another aspect of the invention is directed to a second apparatus for applying an alternating electric field to a living subject. The second apparatus comprises a plurality of conductive regions, a plurality of regions of a dielectric material, a substrate, a plurality of temperature sensors, and at least one electrical conductor. Each of the conductive regions has a front face and a respective area. Each of the regions of the dielectric material, has (i) a respective front face and (ii) a respective rear face disposed against the front face of a respective one of the conductive regions. The substrate is configured to hold the front faces of the plurality of regions of dielectric material on or in the subject's body and support the plurality of conductive regions at respective positions distributed about a centroid. Each of the temperature sensors is disposed in thermal contact with a respective region of the dielectric material. And the at least one electrical conductor is disposed in electrical contact with the plurality of conductive regions. The plurality of conductive regions includes at least one first conductive region and a plurality of second conductive regions, and each of the second conductive regions is positioned more peripherally with respect to the centroid than the at least one first conductive region. A capacitance associated with each of the second conductive regions is at least 10% lower than a capacitance associated with each of the first conductive regions.

In some embodiments of the second apparatus, each of the second conductive regions has an area that is at least 10% less than each of the first conductive regions. In some embodiments of the second apparatus, the regions of the dielectric material disposed against the front face of each of the second conductive regions is at least 10% thicker than the regions of the dielectric material disposed against the front face of each of the first conductive regions. In some embodiments of the second apparatus, the regions of the dielectric material disposed against the front face of each of the second conductive regions have a dielectric constant that is at least 10% lower than the regions of the dielectric material disposed against the front face of each of the first conductive regions.

Another aspect of the invention is directed to a third apparatus for applying an alternating electric field to a living subject. The third apparatus includes a flex circuit, at least one first flexible polymer region, and a plurality of second flexible polymer regions. The flex circuit includes (a) at least one first conductive pad positioned on a front side of the flex circuit, each of the first conductive pads having a first area, (b) a plurality of second conductive pads positioned on the front side of the flex circuit at locations that are peripheral with respect to the at least one first conductive pad, each of the second conductive pads having a respective area that is at least 10% smaller than the first area, and (c) at least one conductive trace disposed in electrical contact with the at least one first conductive pad and the plurality of second conductive pads. The at least one conductive trace is arranged so that each of the first conductive pads and each of the second conductive pads can be driven by an electrical signal. Each of the first flexible polymer regions has a front face, and each of the at least one first flexible polymer regions is disposed over and in front of a respective one of the first conductive pads on the front side of the flex circuit.

Each of the second flexible polymer regions has a front face and is disposed over and in front of a respective one of the second conductive pads on the front side of the flex circuit. At at least one frequency between 100 kHz and 500 kHz, each of the polymer regions has a dielectric constant of at least 20, and each of the polymer regions has a thickness of less than 20 µm in a direction perpendicular to its front face.

Some embodiments of the third apparatus further comprise a plurality of thermistors positioned on a rear side of the flex circuit. In these embodiments, each of the plurality of thermistors is disposed in thermal contact with a respective one of the plurality of second conductive pads, and the flex circuit further includes a plurality of conductive traces that provide access to the plurality of thermistors.

Some embodiments of the third apparatus further comprise a flexible third layer and a layer of conductive hydrogel. In these embodiments, the flexible third layer is configured to support the flex circuit. The flexible third layer has a front face. A first portion of the front face of the flexible third layer is coated with an adhesive that adheres to human skin and is easily removable from the skin. The first portion is positioned outwardly with respect to the flex circuit such that when the first portion is pressed against a region of skin, the adhesive on the first portion will adhere to the skin and hold the plurality of second flexible polymer regions adjacent to the skin. The layer of conductive hydrogel is disposed on the front face of each of the first flexible polymer regions and disposed on the front face of each of the second flexible polymer regions, and the hydrogel is positioned to make contact with the skin when each of the second flexible polymer regions is being held adjacent to the skin by the adhesive.

In some embodiments of the third apparatus, each of the polymer regions has a thickness of less than 5 µm. In some embodiments of the third apparatus, each of the second conductive pads comprises a plurality of conductive subregions that are interconnected by ablatable conductive links.

Some embodiments of the third apparatus further comprise a flexible third layer, a layer of conductive hydrogel, and a plurality of thermistors. The flexible third layer is configured to support the flex circuit. The flexible third layer has a front face. A first portion of the front face of the flexible third layer is coated with an adhesive that adheres to human skin and is easily removable from the skin. The first portion is positioned outwardly with respect to the flex circuit such that when the first portion is pressed against a region of skin, the adhesive on the first portion will adhere to the skin and hold the plurality of second flexible polymer regions adjacent to the skin. The layer of conductive hydrogel is disposed on the front face of each of the first flexible polymer regions and each of the second flexible polymer regions, and the hydrogel is positioned to make contact with the skin when each of the second flexible polymer regions is being held adjacent to the skin by the adhesive. The plurality of thermistors is positioned on a rear side of the flex circuit, and each of the plurality of thermistors is disposed in thermal contact with a respective one of the plurality of second conductive pads. The flex circuit further includes a plurality of conductive traces that provide access to the plurality of thermistors. Optionally, in these embodiments, each of the polymer regions has a thickness of less than 5 µm.

BRIEF DESCRIPTION OF THE DRAWINGS

FIG. 4 depicts a layout for a second embodiment of a transducer array in which the capacitance of the six end elements is lower than the capacitance of the more centrally located elements.

FIGS. 5A and 5B depict front and side (cross-sectional) views of an embodiment that implements a transducer array using a flex circuit.

FIGS. 6A, 6B, and 6C depict front, side (cross-sectional), and exploded views of another embodiment that implements a transducer array using a flex circuit.

FIGS. 7A and 7B depict front and side (cross-sectional) views of another embodiment that implements a transducer array using a flex circuit.

Various embodiments are described in detail below with reference to the accompanying drawings, wherein like reference numerals represent like elements.

DESCRIPTION OF THE PREFERRED EMBODIMENTS

Figure 1:
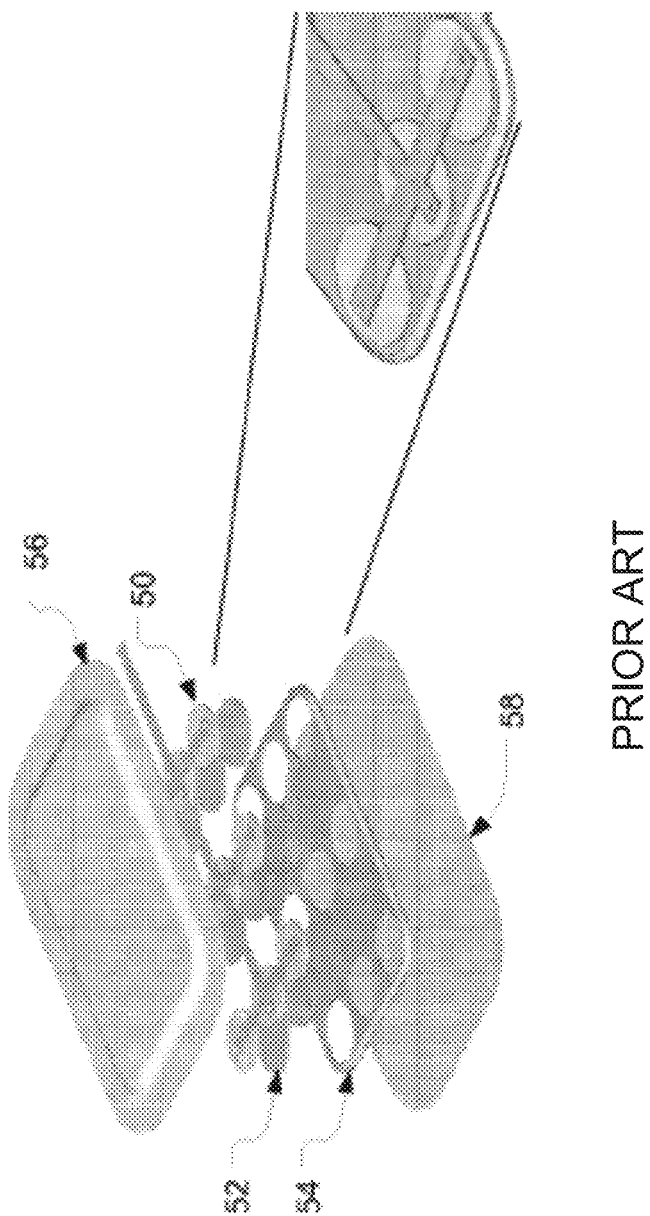
FIG. 1 depicts a prior art transducer array for delivering TTFields.

The electrode elements in transducer arrays used to deliver TTFields to a patient's body may overheat during use, requiring a reduction in voltage to avoid over-shooting the temperature safety threshold (~41° C.). This leads to a reduction in current which can reduce the efficacy of the treatment.

One factor that can be responsible for any given element overheating is a poor connection between the element and the subject's skin, which can occur e.g., if the hydrogel between the electrode element and the skin is melted or disconnected from the skin as a result of reduction in tape adhesion. But after examining the temperature data captured from the 9 element 3×3 transducer arrays, the inventors recognized that another factor was also at work.

More specifically, the inventors obtained temperature data from 80 prior art transducer arrays when those arrays were used to apply TTFields to 20 randomly selected human subjects. Each transducer array had 9 ceramic elements arranged in a 3×3 array, and the construction of all the ceramic elements in any given transducer array was identical. The data included temperature measurements from individual ceramic elements within each transducer array (obtained using thermistors incorporated within the transducer arrays). The temperature measurement data was analyzed to determine which ceramic element within any given transducer array was the first to reach 41.1° C. (in which case a voltage reduction was needed to prevent that element from overheating). This analysis revealed that over 90% of the time, the first ceramic element to reach 41.1° C. was one of the four corner elements. And notably, the difference in temperature between the hottest element and the coolest element in these cases was usually between 3 and 5° C. Computer simulations also suggest that the current flowing through the corner elements is higher than the non-corner elements.

The temperature measurement data was also analyzed to find the average temperature and standard deviation for each disc location. This analysis revealed that the average temperature for the four corner elements was 37.84° C. (standard deviation=1.32; N=639,413 temperature readings), while the average temperature for all non-corner elements that were measured was 37.14° C. (standard deviation=1.15; N=641,708 temperature readings). This means that, on average, the four corner elements ran 0.7° C. hotter than the measured non-corner elements.

The inventor recognized that the corner/end electrode elements of the array running hotter than the non-corner elements is problematic, because when the corner elements run hotter, they will reduce the maximum current that can be delivered by a given transducer array (which can limit the efficacy of the treatment).

The embodiments described herein balance out the average expected temperature increase of the electrode elements in a given transducer array by preemptively reducing the current that flows through the corner/end elements of each transducer array (as compared to the current that flows through the more central elements) in order to preemptively reduce the temperature rise of the corner/end elements. Notably, this reduction in current is not achieved by increasing the ohmic resistance of the corner/end elements (because that would cause $I^2R$ heating). Instead, the reduction in current is achieved by decreasing the capacitance of the corner/end elements (as compared to the capacitance of the more centrally located elements).

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

As used in the specification and the appended claims, the singular forms "a," "an" and "the" include plural referents unless the context clearly dictates otherwise.

Figure 2:
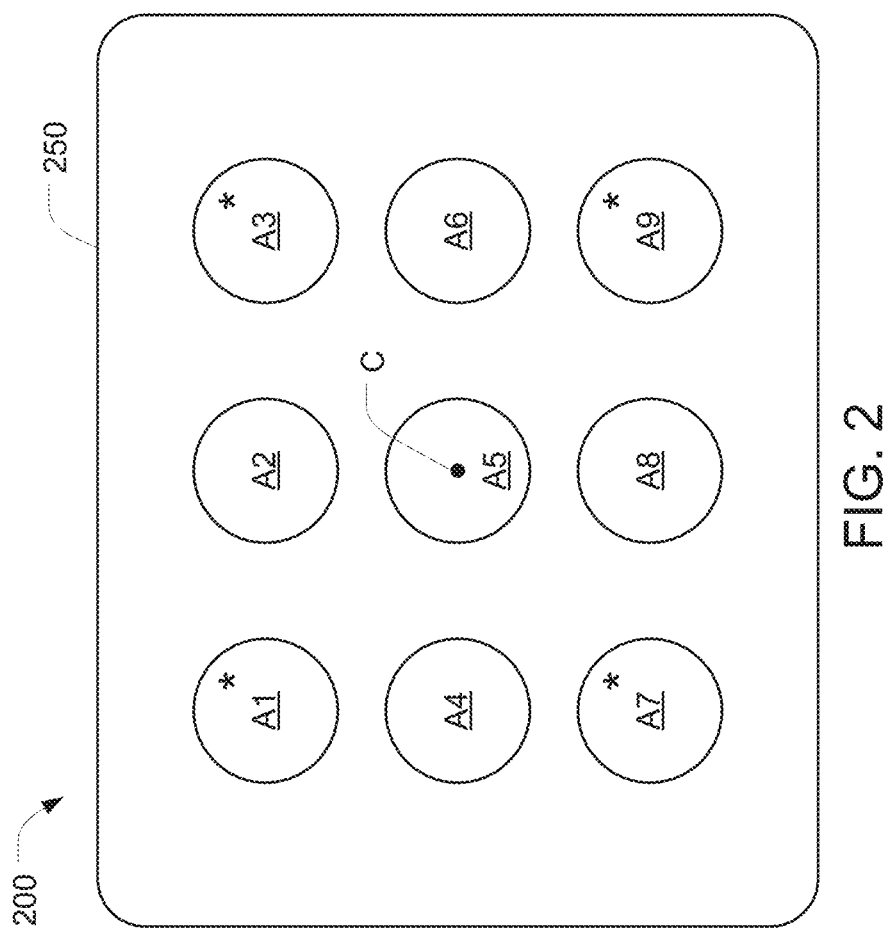
FIG. 2 depicts a layout for a first embodiment of a transducer array in which the capacitance of the four corner elements is lower than the capacitance of the more centrally located elements

FIG. 2 depicts a layout for a first embodiment of a transducer array 200 in which nine round elements A1-A9 made of a dielectric material (e.g., ceramic elements) are arranged in a 3×3 array and supported by a substrate 250. The centroid of all of the elements A1-A9 is labeled "C", and the substrate 250 supports the elements at respective positions distributed about the centroid. In this embodiment, the capacitance of the four corner elements (i.e., A1, A3, A7, and A9, marked with asterisks) is lower than the capacitance of the more centrally located elements A2, A4, A5, A6, and A8. The back of each of the elements A1-A9 has a conductive coating (e.g., is metallized or silvered), and the front of each of the elements A1-A9 is positioned to face the subject during use. Preferably, a layer of hydrogel is disposed between the front face of each of the elements and the subject's skin during use.

One or more electrical conductors (e.g., wiring or traces on a flex circuit, not shown) connects to the metallized backs of each of the elements A1-A9. Preferably, this wiring is configured so that all of the metallized backs are electrically connected to a single conductive wire or trace, which means that the capacitance of all of the elements A1-A9 is arranged in parallel. Temperature sensors (e.g., thermistors, not shown) are preferably positioned in thermal contact with some or all of the elements A1-A9, e.g., similar to the way that the thermistors are positioned in the prior art. The thermal contact between the temperature sensors and the elements may be direct or indirect.

As in the prior art, when a first transducer array 200 is positioned against a person's skin on one side of a person's body, and a second transducer array 200 is positioned against the person's skin on the opposite side of the person's body, and an AC voltage is applied between the leads of the first and second transducer arrays, an electric current is capacitively coupled into the person's body. But the FIG. 2 embodiment differs from the prior art because the capacitance of the corner elements A1, A3, A7, and A9 (which are positioned more peripherally with respect to the centroid C) is lower than the capacitance of the more centrally located elements A2, A4, A5, A6, and A8.

The capacitance of any given ceramic element is (a) proportional to the area of the metallization/silvering on the back side of the ceramic element; (b) proportional to the dielectric constant of the ceramic element; and (c) inversely proportional to the thickness of the ceramic element. Any of these three parameters may be varied to decrease the capacitance of the corner elements as compared to the capacitance of the other elements. The ceramic elements may have a flat and uniform surface, but in alternative embodiments the ceramic elements may not be flat.

Figure 3:
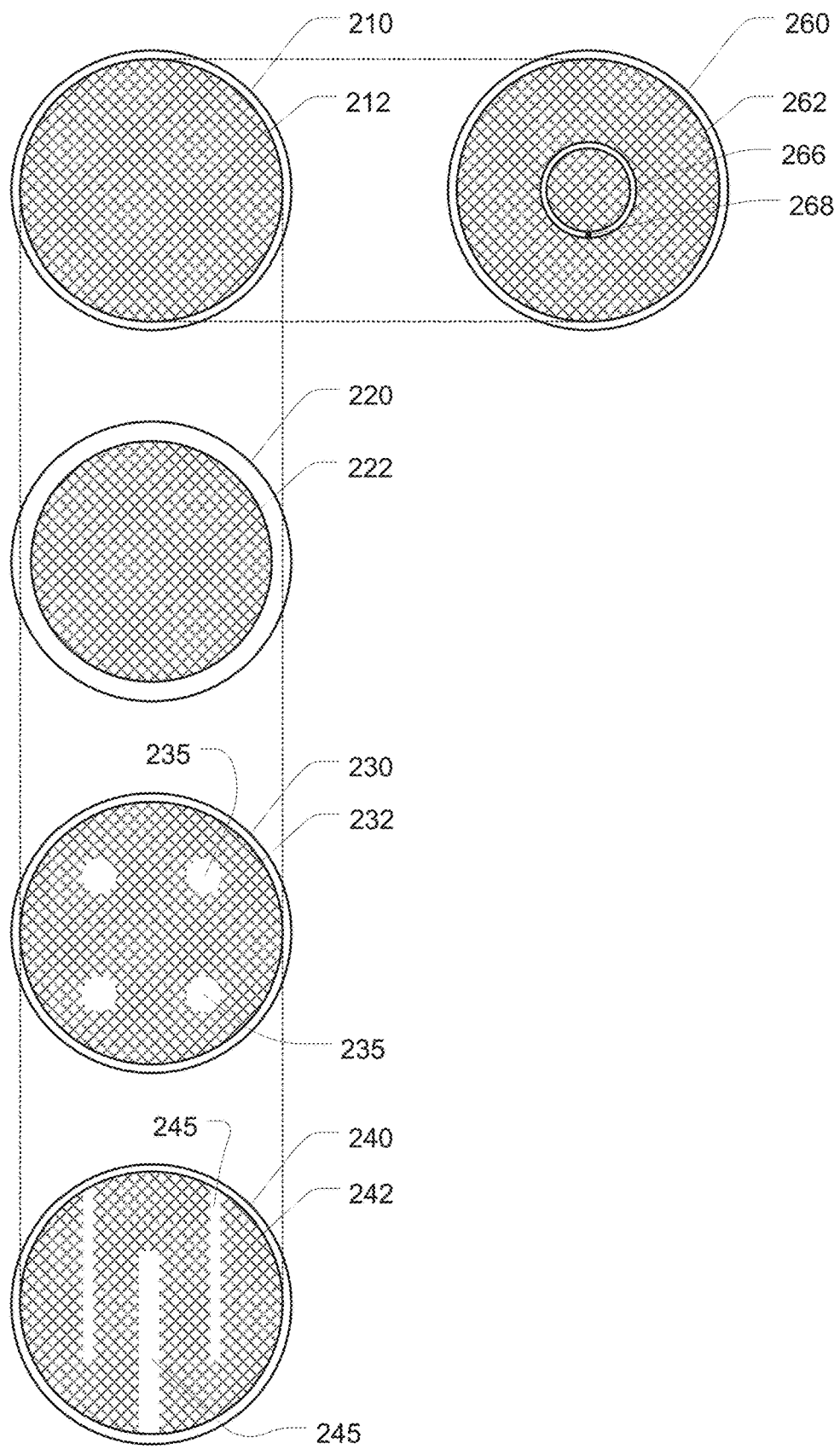
FIG. 3 depicts three different approaches for decreasing capacitance by varying the area of the conductive metallization on the back side of a set of dielectric ceramic elements.

FIG. 3 depicts three different approaches for decreasing the capacitance of the corner elements in FIG. 2 by varying the area of the conductive metallization on the back side of the dielectric ceramic elements. More specifically, the top left panel in FIG. 3 depicts the extent of the metallization 212 on the ceramic element 210 for the central elements A2, A4, A5, A6, and A8 in FIG. 2. The next panel in FIG. 3 depicts a metallization pattern 222 on an element 220 that has a smaller area than the metallization pattern 212. Because the metallization pattern 222 of the element 220 has a smaller diameter than the metallization pattern 212, the capacitance provided by the element 220 will be lower than the capacitance of the element 210. Note that when the metallization pattern 222 is smaller, the diameter of the ceramic element 220 may optionally be reduced.

The next panel in FIG. 3 depicts a different metallization pattern 232 on an element 230 that has a smaller area than the metallization pattern 212. Although both metallization patterns 232 and 212 have the same diameter, because the metallization pattern 232 has round voids 235, the area of the metallization pattern 232 will be smaller than the area of the metallization pattern 212. As a result, the capacitance provided by the element 230 will be lower than the capacitance of the element 210. Similarly, the bottom panel in FIG. 3 depicts yet another metallization pattern 242 on an element 240 that has a smaller area than the metallization pattern 212. Although both metallization patterns 242 and 212 have the same diameter, because the metallization pattern 242 has rectangular voids 245, the area of the metallization pattern 242 will be smaller than the area of the metallization pattern 212. As a result, the capacitance provided by the element 240 will be lower than the capacitance of the element 210.

The ceramic elements depicted in FIG. 3 can therefore be used to create the transducer array depicted in FIG. 2 by using the metallization layout 212 for the central elements A2, A4, A5, A6 and A8, and using any one of the metallization layouts 222, 232, 242 for the corner elements A1, A3, A7, and A9 to provide a lower capacitance at the corner elements. For example, to reduce the capacitance of the corner elements by 10%, the area of metallization in those elements should be reduced by 10%.

Alternatively, the capacitance at the corner elements may be reduced (with respect to the capacitance of the central elements) by keeping the area of metallization constant and using a thicker ceramic element at the four corners. For example, to reduce the capacitance of the corner elements by 10%, the thickness of the ceramic elements at the corners should be 10% higher than the thickness of the central ceramic elements.

As yet another alternative, the capacitance at the corner elements may be reduced (with respect to the capacitance of the central elements) by holding the area of metallization constant and using a ceramic element with a lower dielectric constant at the four corners. For example, to reduce the capacitance of the corner elements by 10%, the dielectric constant of the ceramic elements at the corners should be 10% lower than the dielectric constant of the central ceramic elements.

As yet another alternative, the capacitance at the corner elements may be reduced (with respect to the capacitance of the central elements) by using elements whose capacitance is customizable subsequent to the date of their original manufacture. In this approach, each element is initially manufactured with one or more sub-regions 266 that are connected to a main region 262 by a thin ablatable conductive link 268. In the elements initial state, the area of the metallization of the element is the sum of the areas of the main region 262 and the subregions 266.

At some point subsequent to the initial manufacture of the elements, the capacitance of the corner elements is reduced by ablating the conductive links 268. Ablation of the links 268 may be accomplished using a variety of alternative approaches, e.g., blasting them with a laser or passing a sufficiently high current through the link 268 (similar to blowing a fuse). After ablation of those links, the corresponding subregions 266 in the corner elements are effectively disconnected from the circuit, which reduces the active area of the corner elements. And because the conductive links 268 for the central elements are not ablated, the central elements will have a higher active area (and a corresponding higher capacitance) than the corner elements.

Returning to FIG. 2, assume that a first transducer array 200 is positioned against a person's skin on one side of a person's body, and a second transducer array 200 is positioned against the person's skin on the opposite side of the person's body, and an AC voltage is applied between the leads of the first and second transducer arrays. Further assume that the capacitance of the corner elements A1, A3, A7, and A9 is 10% lower than the capacitance of the central elements A2, A4, A5, A6 and A8. (The decrease in capacitance may be effectuated using any of the approaches described above.) In this situation, the current that is coupled through the corner elements will be approximately 10% lower than it would have been if the capacitance of the corner elements was the same as the capacitance of the central elements. And this reduction in current at the corner elements will lower the temperature of the corner elements.

Let us now analyze the benefit that flows from reducing the capacitance of the corner elements. We begin, for purposes of comparison, by looking at the prior art situation in which all the elements are driven by an AC voltage with an amplitude X, and the capacitance of all the elements in the transducer array is the same. Assume that, during operation, the temperature of the corner elements of the prior art transducer array reaches 41° C., but the temperature of the non-corner elements is only 39° C. Under these circumstances, the corner elements are handling the highest possible current that avoids overheating. But because the non-corner elements are operating below 41° C., they are necessarily handling less current than they could safely handle without overheating.

Assume now the FIG. 2 situation in which all the elements are driven by an AC voltage with the same amplitude X, but the capacitance of the corner elements in the transducer array has been reduced by whatever percentage is necessary to lower the temperature of the corner elements by 2° C. Under these circumstances, all of the elements in the transducer array 200 would be operating at 39° C., which means that all of the elements are handling less current than they could safely handle without overheating.

Because all of the elements are handling less current than they can safely handle, the voltage amplitude can be increased beyond X to whatever amplitude raises the temperature of the corner elements to 41° C. At this point, the corner elements will be handling the same current that they were handling in the prior art situation described above. But because the non-corner elements in the FIG. 2 embodiment are now being driven by a higher voltage, the non-corner elements in the FIG. 2 embodiment will be handling more current than the non-corner elements in the prior art situation. This means that the total current being handled by the FIG. 2 transducer array (i.e., the sum of the currents being handled by the corner elements and the non-corner elements) will be higher than the total current that was handled in the prior art situation. And this increase in current can improve the efficacy of the treatment.

FIG. 4 depicts a layout for a second embodiment of a transducer array 200' in which 13 round elements B1-B13 made of a dielectric material (e.g., ceramic elements) are arranged in three rows and supported by a substrate 250. The centroid of all of the elements B1-B13 is labeled "C", and the substrate 250 supports the elements at respective positions distributed about the centroid. The construction and use of the FIG. 4 embodiment is similar to the construction and use of the FIG. 2 embodiment described above, except that in the FIG. 4 embodiment, the capacitance of the six end elements (i.e., B1, B4, B5, B9, B10, and B13, marked with asterisks) is lower than the capacitance of the more centrally located elements B2, B3, B6-B8, B11, and B12. Any of the approaches described above for reducing the capacitance of the corner elements in the FIG. 2/3 embodiment may be used for reducing the capacitance of the end elements in any given row in this FIG. 4 embodiment. For each of these approaches, the current may be balanced by controlling the capacitance of each electrode element or by varying the capacitance of groups of electrode elements within a given array, which may be achieved using two, three, or more than three different groups of electrode elements.

The reduction in capacitance of the end elements in any given row will result in a corresponding decrease in current, which will lower the temperature of the end elements (as compared to a transducer array in which the capacitance of all the elements is the same). The benefits that flow from reducing the capacitance of the end elements in this FIG. 4 embodiment are similar to the benefits that flow from reducing the capacitance of the corner elements in the FIG. 2 embodiment.

Note that while round pieces of a ceramic dielectric material with a layer of metal disposed on its rear face serve as the electrode elements in the FIGS. 2-4 embodiments described above, the electrode elements need not be round, and alternative shapes (e.g., flat square or hexagonal pieces of a ceramic dielectric material) could also be used.

Moreover, the techniques described above of reducing the capacitance of electrode elements in the corners of a transducer array (see, e.g., FIG. 2) or reducing the capacitance of the electrode elements at both ends of each row in a transducer array (see, e.g., FIG. 4) is not limited to electrode elements constructed using a ceramic dielectric material with a layer of metal disposed on its rear face. To the contrary—the technique of reducing the capacitance of electrode elements in the corners of a transducer array or at the ends of each row in a transducer array can be applied to transducer arrays built using a variety of alternative constructions.

Some examples of alternative approaches for constructing transducer arrays will now be described in connection with FIG. 5-7, followed by a description of how the capacitance of the corner/end elements can be varied when those versions of transducer arrays are used.

The embodiments described below in connection with FIG. 5-7 rely on recently discovered polymer compositions that have significantly higher dielectric constants than conventional polymers. More specifically, the dielectric constant of these recently discovered polymer compositions is high enough to build a transducer array that can effectively capacitively couple an AC signal into a person's body through a polymer insulating layer. Note that in all embodiments described herein, the front of an electrode or transducer array is the side that faces the person's body, and the rear of the electrode or transducer array is the opposite side.

FIGS. 5A and 5B depict front and side (cross-sectional) views of an embodiment that implements a transducer array using a flex circuit. This embodiment is used for applying TTFields to a living subject. This FIG. 5 embodiment has a flex circuit that includes (a) a plurality of conductive pads 20 (e.g., copper pads) positioned on a front side of the flex circuit 25. Each of the conductive pads 20 has an area. At least one conductive trace (not shown) is disposed in electrical contact with the plurality of conductive pads 20. The at least one conductive trace is arranged so that each of the conductive pads 20 can be driven by an electrical signal.

This embodiment also has a plurality of flexible polymer regions 30. These flexible polymer regions 30 could be regions within a single contiguous sheet of polymer material, as depicted in FIG. 5A. Alternatively, these regions 30 could be discrete sections (or "islands") of flexible polymer that are separated by gaps. Each of the flexible polymer regions 30 has a front face and is disposed over and in front of a respective one of the conductive pads 20 on the front side of the flex circuit 25.

Specifications for the polymer regions 30 in this embodiment are as follows: (1) at at least one frequency between 100 kHz and 500 kHz, each of the polymer regions 30 has a dielectric constant of at least 20; and (2) each of the polymer regions 30 has a thickness of less than 20 µm in a direction perpendicular to its front face. In some embodiments, the thickness of each of the polymer regions 30 multiplied by its dielectric strength is at least 50 V, and in some embodiments this value is at least 200 V. For example, if the thickness is 10 µm and the dielectric strength is 30 MV/m, then this value will be 300 V.

In some preferred embodiments, the polymer regions 30 comprise poly(vinylidene fluoride-trifluoroethylene-chlorotrifluoroethylene) and/or poly(vinylidene fluoride-trifluoroethylene-1-chlorofluoroethylene). Those two polymers are abbreviated herein as "Poly(VDF-TrFE-CtFE)" and "Poly(VDF-TrFE-CFE)", respectively. These embodiments are particularly advantageous because the dielectric constant of these materials is on the order of 40. Because the TTFields are capacitively coupled through the electrode 10, and because capacitance is inversely proportional to the thickness of the dielectric layer, the polymer regions 30 are preferably as thin as possible (e.g., less than 10 µm or less than 5 µm). On the other hand, the polymer regions 30 should not be too thin because that could impair manufacturability, compromise the layer's structural integrity, and risk dielectric breakdown when the AC signals are applied. In some embodiments, the polymer regions 30 have a thickness that is at least 1 µm. In some embodiments the polymer regions 30 are between 1-5 µm thick, or between 1-3 µm thick (e.g., about 2 µm), which provides a good balance between the parameters noted above. In some embodiments, the thickness of the polymer regions 30 is uniform. But in alternative embodiments (e.g., as described below), the thickness could be non-uniform.

Optionally, ceramic nanoparticles may be mixed into the Poly(VDF-TrFE-CtFE) and/or Poly(VDF-TrFE-CFE) to form a "nanocomposite." Optionally, these ceramic nanoparticles may comprise ferroelectric metal oxides (e.g., at least one of barium titanate and barium strontium titanate).

In alternative embodiments, instead of forming the polymer regions 30 from Poly(VDF-TrFE-CtFE) and/or Poly(VDF-TrFE-CFE), a different polymer that provides a high level of capacitance may be used. The requirements for these different polymers are as follows: (1) at at least one frequency between 100 kHz and 500 kHz, the polymer layer has a dielectric constant of at least 20; and (2) the polymer layer has a thickness of less than 20 µm in a direction perpendicular to the front face of the polymer layer. In some embodiments, the thickness of the polymer layer multiplied by its dielectric strength is at least 50 V, and in some embodiments this value is at least 200 V. Note that the values for dielectric constant and breakdown voltage specified herein are specified within a temperature range of 30–42° C., and the values of those parameters outside that temperature range are less relevant.

Examples of alternative polymers that may be used in place of Poly(VDF-TrFE-CtFE) and/or Poly(VDF-TrFE-CFE) include the following: (1) ceramic nanoparticles mixed into at least one of Poly(VDF-TrFE), P(VDF-HFP), PVDF, or other polymers; and (2) barium titanate and/or barium strontium titanate ceramic nanoparticles mixed into at least one of Poly(VDF-TrFE), P(VDF-HFP), PVDF (where Poly(VDF-TrFE), P(VDF-HFP) and PVDF are, respectively, poly(vinylidene fluoride-trifluoroethylene), poly(vinylidene fluoride-hexafluoropropylene), and polyvinylidene fluoride). In other embodiments, the polymer regions 30 are formed by mixing ceramic nanoparticles into at least one other polymer (i.e., a polymer not listed above in this paragraph).

In this FIG. 5 embodiment, the plurality of polymer regions 30 can be printed, sprayed, or cast directly onto the plurality of conductive pads 20, which makes it much easier to obtain a very thin polymer layer. In some embodiments (e.g., in those where the polymer regions 30 are printed, sprayed, or cast directly onto the conductive pads 20), the polymer regions have a thickness of less than 5 µm.

Increasing the total area that is covered by the conductive pads 20 will increase the capacitance of the overall device. In some embodiments, the areas of the plurality of conductive pads 20 collectively add up to at least 25 cm$^2$.

The FIG. 5 embodiments may be affixed to a person's skin using a flexible third layer that resembles a bandage. In these embodiments, a flexible third layer 40 is positioned behind the flex circuit 25. The flexible third layer 40 has a front face. At least a portion of the front face of the third layer 40 is coated with an adhesive. A first region of the adhesive is positioned directly behind the flex circuit 25 and supports the flex circuit 25, and a second region of the adhesive is positioned outwardly with respect to the first region. (This is the portion that is not covered by the flex circuit in FIG. 5A.) This second region is configured to, when pressed against a region of skin, adhere to the skin and hold the plurality of polymer regions 30 adjacent to the skin. The adhesive used in the second region should also be easily removable from the skin. Although the flexible third layer 40 holds the plurality of polymer regions 30 adjacent to the skin, a layer of conductive hydrogel 50 may be interposed between the polymer regions 30 and the skin, and the relationship between the polymer regions 30 and the skin would nevertheless be considered "adjacent." (This applies to this FIG. 5 embodiment as well as to other embodiments described herein). In this situation, the layer of hydrogel 50 is disposed on the front face of each of the polymer regions 30. The hydrogel 50 is positioned to make contact with the skin when each of the polymer regions 30 is being held adjacent to the skin by the second region of the adhesive.

In a variation of the FIG. 5 embodiments, a different approach is used to hold the polymer regions adjacent to the skin using a flexible third layer. In these embodiments, the flexible third layer is configured to support the flex circuit. The flexible third layer has a front face, and optionally can include a plurality of cut-out open regions that correspond to the positions of the conductive pads 20. A first portion of the front face of the flexible third layer is coated with an adhesive that adheres to human skin and is easily removable from the skin. This first portion is positioned outwardly with respect to the flex circuit 25 such that when the first portion is pressed against a region of skin, the adhesive on the first portion will adhere to the skin and hold the plurality of polymer regions 30 adjacent to the skin. As in the previous embodiments, a layer of conductive hydrogel 50 may be disposed on the front face of each of the polymer regions 30. The hydrogel 50 is positioned to make contact with the skin when each of the polymer regions 30 is being held adjacent to the skin by the adhesive.

A plurality of thermistors may be incorporated into this FIG. 5 embodiment. One way to accomplish this is to position the plurality of thermistors 60 on the rear side of the flex circuit 25 (i.e., between the flex circuit 25 and the flexible third layer 40), with each of the plurality of thermistors 60 positioned in thermal contact with a respective one of the plurality of conductive pads 20. In these embodiments, the flex circuit 25 further includes a plurality of conductive traces that provide access to the plurality of thermistors 60. In alternative embodiments (not shown), the thermistors 60 could be positioned between the conductive pads 20. However, in this case an additional insulation should be provided in front of the thermistors.

FIGS. 6A, 6B, and 6C depict front, side (cross-sectional), and exploded views of another embodiment that implements a transducer array using a flex circuit. This embodiment is also used for applying TTFields to a living subject. But instead of using conductive pads that are integrated into the flex circuit (as in the FIG. 5 embodiment described above), the FIG. 6 embodiments relies on a plurality of pieces of metal foil that are positioned in front of the flex circuit and electrically connected to respective pads of the flex circuit.

The FIG. 6 embodiment has a flex circuit 145 that includes (a) a plurality of conductive pads 140 positioned on a front side of the flex circuit 145, and (b) at least one conductive trace (not shown) disposed in electrical contact with the plurality of conductive pads 140. The at least one conductive trace is arranged so that each of the conductive pads 140 can be driven by an electrical signal. A plurality of pieces of metal foil 120 are positioned in front of the flex circuit 145, and each of those pieces 120 has a front face having an area. Each of the pieces 120 is electrically connected to a respective one of the conductive pads 140.

The electrical connection between each of the pieces 120 and a respective one of the conductive pads 140 may be implemented as depicted in FIG. 6B by positioning an insulating layer 130 between each of the pieces 120 and the corresponding conductive pad 140. The insulating layer 130 in this FIG. 6B embodiment has an opening behind each of the plurality of pieces of metal foil 120 and a conductive path (e.g., metal, solder, etc.) is provided through this opening.

All variations of the FIG. 6 embodiment also have a plurality of flexible polymer regions 30, each of which has a front face and is disposed over and in front of a respective one of the plurality of pieces of metal foil 120. Specifications for the polymer regions 30 in this embodiment are as follows: (1) at at least one frequency between 100 kHz and 500 kHz, each of the polymer regions 30 has a dielectric constant of at least 20; and (2) each of the polymer regions 30 has a thickness of less than 20 µm in a direction perpendicular to its front face. In some embodiments, the thickness of each of the polymer regions 30 multiplied by its dielectric strength is at least 50 V, and in some embodiments this value is at least 200 V. Any of the polymer materials discussed above in connection with the FIG. 5 embodiments may be used to implement the polymer regions 30 in this FIG. 6 embodiment.

In this FIG. 6 embodiment, the plurality of polymer regions 30 can be printed, sprayed, or cast directly onto the pieces of metal foil 120, which makes it much easier to obtain a very thin polymer layer. In some embodiments (e.g., in those embodiments where the polymer regions 30 are printed, sprayed, or cast directly onto the pieces of metal foil 120), the polymer regions have a thickness of less than 5 µm.

Increasing the total area that is covered by the pieces of metal foil 120 will increase the capacitance of the overall device. In some embodiments, the areas of the plurality of pieces of metal foil collectively add up to at least 25 cm².

The FIG. 6 embodiments may be affixed to a person's skin using a flexible third layer 40, the nature of which is similar to the flexible third layer described above in connection with the FIG. 5 embodiments. Additionally, a layer of conductive hydrogel 50 may be disposed on the front face of each of the polymer regions, as described above in connection with the FIG. 5 embodiments.

A plurality of thermistors may also be incorporated into this FIG. 6 embodiment, as described above in connection with the FIG. 5 embodiments.

FIGS. 7A and 7B illustrate an embodiment that is similar to the FIG. 6 embodiment described above, except that it uses an alternative approach for implementing the electrical connection between each of the pieces of metal foil 120 and a respective one of the conductive pads 140. As in the FIG. 6 approach, an insulating layer 130 is positioned between each of the pieces 120 and the corresponding conductive pad 140. But the insulating layer 130 in this FIG. 7 embodiment does not have openings behind each of the plurality of pieces of metal foil 120. Instead, the insulating layer 130 in this FIG. 7 embodiment is continuous. The electrical connection between each of the pieces of metal foil 120 and the conductive pads 140 of the flex circuit is made using a side or edge electrical connection 160 between the conductive pads 140 and the pieces of metal foil 120.

To use the transducer arrays depicted in any of FIGS. 5-7, a pair of transducer arrays are affixed to the person's skin on opposite sides of a target region in the person's body, and an AC voltage is applied between those two transducer arrays. Each of the conductive pads 20 (in the FIG. 5 embodiment) or the pieces of metal foil 120 (in the FIG. 6-7 embodiments) acts as the plate of an individual capacitor, and each of the corresponding polymer regions 30 acts as the insulating layer of that capacitor. An AC electric field will then be capacitively coupled through those capacitors into the person's body.

When all of those capacitors have the same capacitance, one would expect the temperature of the corner/end pads 20 (or pieces of metal foil 120) to overheat more often than the more centrally located pads/pieces for the same reasons as in the prior art transducer arrays depicted in FIG. 1. But if the capacitance of the corner/end pads 20 (or pieces 120) in the FIGS. 5-7 embodiments is reduced with respect to the more centrally located pads/pieces, the temperature among all the pads 20 (or pieces 120) of any given transducer array may be equalized for the same reasons as in the FIG. 2-4 embodiments described above.

Figure 8:
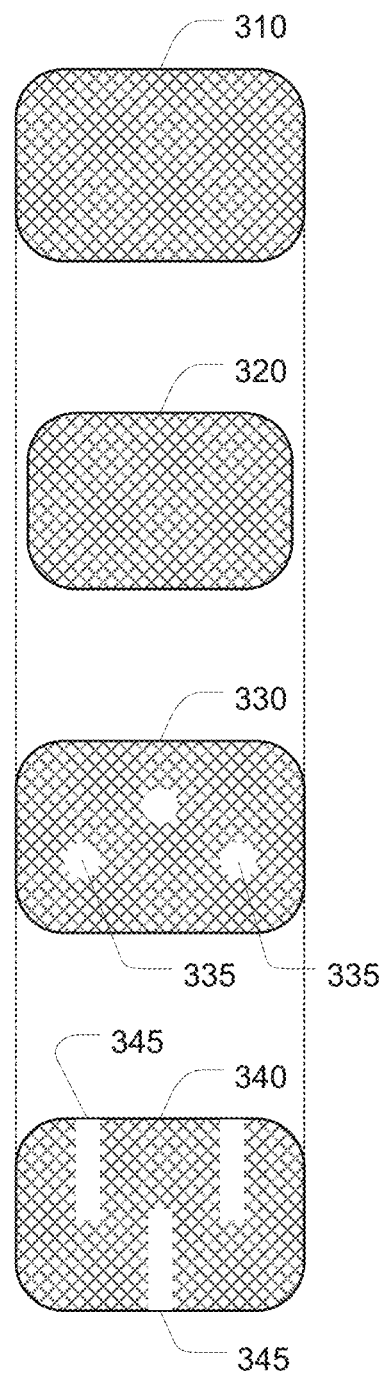
FIG. 8 depicts approaches for decreasing capacitance by reducing the area of PCB pads (or pieces of metal) that serve as the plate of a capacitor by incorporating voids into the PCB pads (or pieces of metal).

FIG. 8 depicts one approach for reducing the capacitance of the corner/end pads 20 (or pieces 120) in the FIG. 5-7 embodiments by using pads (or pieces) that have a smaller area at the corners/ends of the transducer array (as compared to the more centrally located portions of the transducer array). More specifically, if the more centrally located pads 20 (or pieces 120) have an area that resembles the upper region 310, and the more peripherally located pads 20 (or pieces 120) have areas that resemble the region 320 (which is smaller than the region 310), the region 330 (which has circular voids 335) or the lower region 340 (which has rectangular voids 345), then the area of the more peripherally located pads 20 (or pieces 120) will be smaller than the area of the more centrally located pads 20 (or pieces 120). Because the pads 20 (or pieces 120) operate as the plates of capacitors, the reduction in area will result in a reduction of capacitance of the more peripherally located pads 20 (or pieces 120) with respect to the more centrally located pads 20 (or pieces 120). This will reduce the current that flows through the more peripherally located pads 20 (or pieces 120), which will lower the temperature at those pads 20 (or pieces 120).

Figure 9:
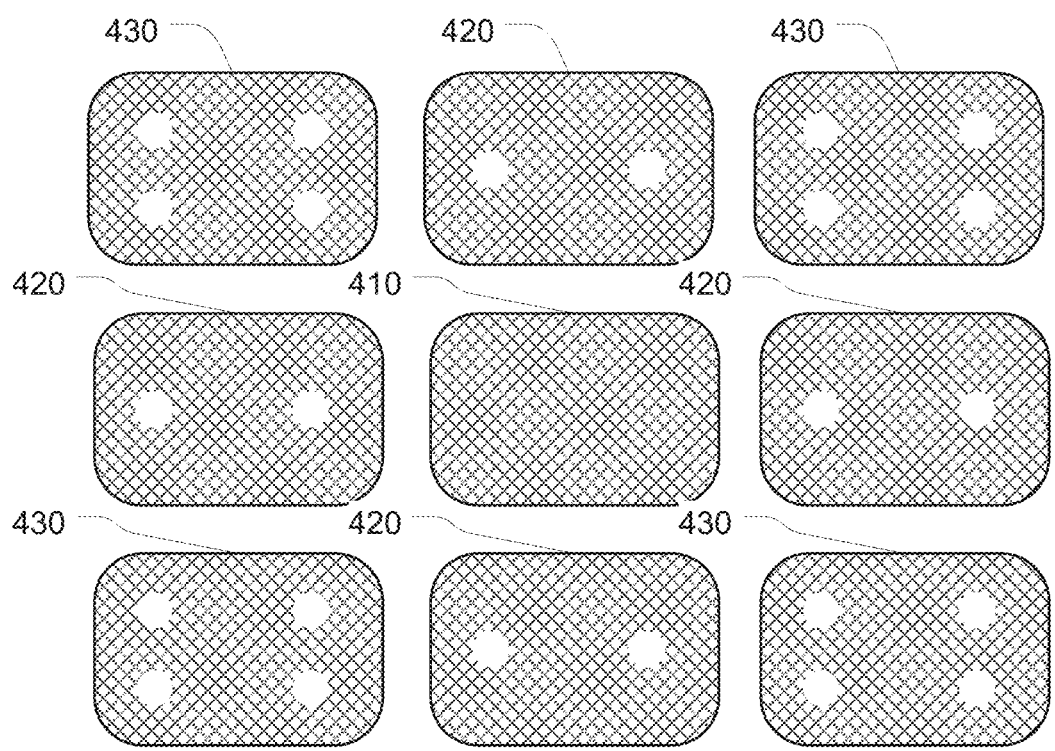
FIG. 9 depicts a PCB pad layout that provides lower capacitance for the more peripherally located pads.

FIG. 9 depicts one example of a suitable layout for the PCB pads in the FIG. 5-7 embodiments that provides higher capacitance for the more centrally located pads and lower capacitance for the more peripherally located pads, by customizing the patterns of the printed circuit pads. More specifically, in this example, the center pad 410 has 100% area coverage to provide the maximum amount of capacitance; the top, bottom, right, and left pads 420 have a smaller percentage of area coverage to provide a lower level of capacitance; and the corner pads 430 have a still smaller percentage of area coverage to provide a still lower level of capacitance. Optionally, the electric field distribution for any given patient may be controlled by custom-designing the pattern of area coverage for each printed circuit pad and/or the layouts and sizes of those pads when the flex circuit is manufactured. Accordingly, the current may be balanced by using pads of varying area coverages within a given array, which may be achieved using two, three, or more than three different area sizes.

Figure 10:
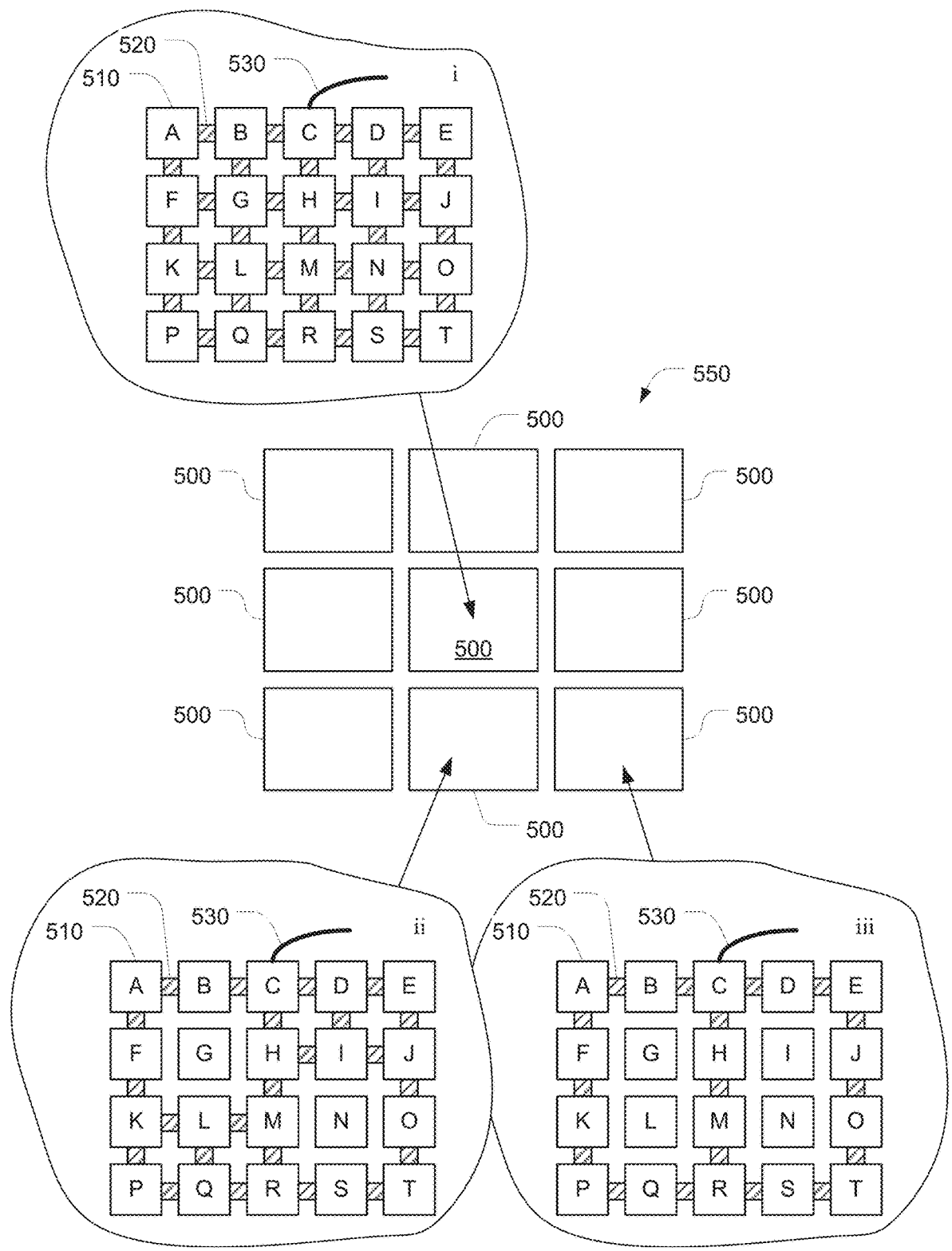
FIG. 10 depicts an alternative approach for reducing the capacitance of specific regions of a flex circuit by ablating thin conductive links.

FIG. 10 depicts an alternative approach for changing the pattern of area coverage that is provided by any given pad of a flex circuit subsequent to the date of the original manufacturer of the flex circuit. In this approach, the flex circuit is initially manufactured with a plurality of regions 500, each of which has a plurality of sub-regions 510 that are interconnected by thin ablatable conductive links 520 (as depicted in detail i in FIG. 10), and an AC voltage is applied to a single one of those subregions 510 by a lead 530. Note that although there are nine regions 500 arranged in a 3×3 array 550 in the example depicted in FIG. 10, the number of regions 500 may vary (e.g., between 9 and 30), as can the arrangement of those regions 500.

At some point subsequent to the initial manufacture of the flex circuit, a selected number of subregions 510 are disconnected by ablating the conductive links 520 that lead to those subregions 510. For example, in detail ii, all the links that lead to the subregions 510 labeled G and N have been ablated. And in detail iii, all the links that lead to the subregions 510 labeled G, I, L, and N have been ablated. Ablation of the links 520 may be accomplished using a variety of alternative approaches, e.g., blasting them with a laser or passing a sufficiently high current through the link 520 (similar to blowing a fuse). After ablation of those links, the corresponding subregions 510 are effectively disconnected from the circuit, which reduces the active area, which reduces the capacitance of the corresponding region 500.

This approach can be used to reduce the capacitance of the regions positioned in the corner of any given array (as described above) by ablating specific links 520 within the regions 500 positioned in the corners of the overall array 550. And advantageously, this approach can be used at a time that is subsequent to the initial manufacture of the flex circuit (e.g., to customize the capacitance of portions of the overall array 550 to match the needs of an individual patient).

Other approaches for reducing the capacitance of the corner/end pads 20 (or pieces 120) may also be used, including reducing the capacitance of those pads or pieces by increasing the thickness or decreasing the dielectric constant of the corresponding polymer regions 30. In each case, this approach can be used to balance the current by using pads having varying thickness of the polymer regions within a given array, or by using pads having varying dielectric constant of the polymer regions within a given array, which may be achieved using two, three, or more than three different variations in thickness or dielectric constant, respectively.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for applying an alternating electric field to a living subject, the apparatus comprising:
    a plurality of conductive regions, each of the plurality of conductive regions having a front face and a respective area;
    a plurality of regions of a dielectric material, each of which has (i) a respective front face and (ii) a respective rear face disposed against the front face of a respective one of the plurality of conductive regions;
    a substrate configured to hold the front faces of the plurality of regions of the dielectric material on or in the living subject's body and support the plurality of conductive regions at respective positions distributed about a centroid; and
    at least one electrical conductor disposed in electrical contact with the plurality of conductive regions, wherein the plurality of conductive regions includes at least one first conductive region and a plurality of second conductive regions, wherein each of the plurality of second conductive regions is positioned more peripherally with respect to the centroid than the at least one first conductive region, and wherein an area of each of the plurality of second conductive regions is at least 10% smaller than an area of each of the at least one first conductive region.

2. The apparatus of claim 1, wherein each of the plurality of regions of the dielectric material comprises a ceramic disk, and wherein each of the plurality of the conductive regions comprises a layer of metal disposed on the rear face of a respective one of the ceramic disks.

3. The apparatus of claim 1, wherein each of the plurality of regions of the dielectric material comprises a flat piece of ceramic material, and wherein each of the plurality of the conductive regions comprises a layer of metal disposed on the rear face of a respective one of the flat pieces of ceramic material.

4. The apparatus of claim 1, wherein each of the plurality of the conductive regions comprises a pad of a printed circuit, and wherein each of the plurality of regions of the dielectric material comprises a polymer film.

5. The apparatus of claim 1, wherein each of the plurality of the conductive regions comprises a pad of a printed circuit, and wherein each of the plurality of regions of the dielectric material is implemented using a different section of a single, contiguous, polymer film.

6. The apparatus of claim 1, wherein each of the plurality of the conductive regions comprises a layer of metal foil, and wherein each of the plurality of regions of the dielectric material comprises a polymer film.

7. The apparatus of claim 1, wherein each of the plurality of the conductive regions comprises a layer of metal foil, and wherein each of the plurality of regions of the dielectric material is implemented using a different section of a single, contiguous, polymer film.

8. The apparatus of claim 1, further comprising an adhesive layer configured to hold the substrate against the living subject's skin so that the front faces of the plurality of regions of dielectric material face the living subject's body.

9. The apparatus of claim 1, wherein the plurality of conductive regions further comprises:
    a plurality of third conductive regions, wherein each of the plurality of third conductive regions is positioned more peripherally with respect to the centroid than the plurality of second conductive regions, and wherein an area of each of the plurality of third conductive regions is at least 10% smaller than the area of each of the plurality of second conductive regions.

10. An apparatus for applying an alternating electric field to a living subject, the apparatus comprising:
a plurality of conductive regions, each of the plurality of conductive regions having a front face and a respective area;
a plurality of regions of a dielectric material, each of which has (i) a respective front face and (ii) a respective rear face disposed against the front face of a respective one of the plurality of conductive regions;
a substrate configured to hold the front faces of the plurality of regions of the dielectric material on or in the living subject's body and support the plurality of conductive regions at respective positions distributed about a centroid;
a plurality of temperature sensors, each of which is disposed in thermal contact with a respective region of the plurality of regions of the dielectric material; and
at least one electrical conductor disposed in electrical contact with the plurality of conductive regions, wherein the plurality of conductive regions includes at least one first conductive region and a plurality of second conductive regions, wherein each of the plurality of second conductive regions is positioned more peripherally with respect to the centroid than the at least one first conductive region, and wherein a capacitance associated with each of the plurality of second conductive regions is at least 10% lower than a capacitance associated with each of the at least one first conductive region.

11. The apparatus of claim 10, wherein each of the plurality of second conductive regions has an area that is at least 10% less than each of the at least one first conductive region.

12. The apparatus of claim 10, wherein the plurality of regions of the dielectric material disposed against the front face of each of the plurality of second conductive regions is at least 10% thicker than the regions of the plurality of dielectric material disposed against the front face of each of the at least one first conductive region.

13. The apparatus of claim 10, wherein the plurality of regions of the dielectric material disposed against the front face of each of the plurality of second conductive regions have a dielectric constant that is at least 10% lower than the plurality of regions of the dielectric material disposed against the front face of each of the at least one first conductive region.

14. An apparatus for applying an alternating electric field to a living subject, the apparatus comprising:
a flex circuit that includes (a) at least one first conductive pad positioned on a front side of the flex circuit, each of the at least one first conductive pad having a first area, (b) a plurality of second conductive pads positioned on the front side of the flex circuit at locations that are peripheral with respect to the at least one first conductive pad, each of the plurality of second conductive pads having a respective area that is at least 10% smaller than the first area, and (c) at least one conductive trace disposed in electrical contact with the at least one first conductive pad and the plurality of second conductive pads, wherein the at least one conductive trace is arranged so that each of the at least one first conductive pad and each of the plurality of second conductive pads can be driven by an electrical signal;
at least one first flexible polymer region each of which has a front face, and is disposed over and in front of a respective one of the at least one first conductive pads on the front side of the flex circuit; and
a plurality of second flexible polymer regions, each of which has a front face and is disposed over and in front of a respective one of the plurality of second conductive pads on the front side of the flex circuit,
wherein, at least one frequency between 100 KHz and 500 kHz, each of the at least one first flexible polymer region and the plurality of second flexible polymer regions has a dielectric constant of at least 20, and
wherein each of the at least one first flexible polymer region and the plurality of second flexible polymer regions has a thickness of less than 20 µm in a direction perpendicular to the front face of the at least one first flexible polymer region and the front face of the plurality of second flexible polymer regions.

15. The apparatus of claim 14, further comprising a plurality of thermistors positioned on a rear side of the flex circuit, wherein each of the plurality of thermistors is disposed in thermal contact with a respective one of the plurality of second conductive pads,
wherein the flex circuit further includes a plurality of conductive traces that provide access to the plurality of thermistors.

16. The apparatus of claim 14, further comprising:
a flexible third layer configured to support the flex circuit, the flexible third layer having a front face, wherein (a) a first portion of the front face of the flexible third layer is coated with an adhesive that is configured to adhere to the living subject's skin and be removable from the living subject's skin, and (b) the first portion is positioned outwardly with respect to the flex circuit and is configured such that when the first portion is pressed against a region of the living subject's skin, the adhesive on the first portion is configured to adhere to the living subject's skin and hold the plurality of second flexible polymer regions adjacent to the living subject's skin; and
a layer of conductive hydrogel disposed on the front face of each of the at least one first flexible polymer regions and on the front face of each of the plurality of second flexible polymer regions, wherein the layer of conductive hydrogel is configured to make contact with the living subject's skin when each of the plurality of second flexible polymer regions is being held adjacent to the living subject's skin by the adhesive.

17. The apparatus of claim 14, wherein each of the at least one first flexible polymer region and the plurality of second flexible polymer regions has a thickness of less than 5 µm.

18. The apparatus of claim 14, wherein each of the plurality of second conductive pads comprises a plurality of conductive sub-regions that are interconnected by ablatable conductive links.

19. The apparatus of claim 14, further comprising:
a flexible third layer configured to support the flex circuit, the flexible third layer having a front face, wherein (a) a first portion of the front face of the flexible third layer is coated with an adhesive that is configured to adhere to the living subject's skin and be removable from the living subject's skin, and (b) the first portion is positioned outwardly with respect to the flex circuit and is configured such that when the first portion is pressed against a region of the living subject's skin, the adhesive on the first portion is configured to adhere to the living subject's skin and hold the plurality of second flexible polymer regions adjacent to the living subject's skin; and
a layer of conductive hydrogel disposed on the front face of each of the at least one first flexible polymer regions and each of the plurality of second flexible polymer regions, wherein the layer of conductive hydrogel is configured to make contact with the living subject's skin when each of the plurality of second flexible polymer regions is being held adjacent to the living subject's skin by the adhesive; and a plurality of thermistors positioned on a rear side of the flex circuit, wherein each of the plurality of thermistors is disposed in thermal contact with a respective one of the plurality of second conductive pads, wherein the flex circuit further includes a plurality of conductive traces that provide access to the plurality of thermistors.

20. The apparatus of claim 19, wherein each of the at least one first flexible polymer region and the plurality of second flexible polymer regions has a thickness of less than 5 μm.

* * * * *